(12) United States Patent
Huang et al.

(10) Patent No.: US 11,782,036 B2
(45) Date of Patent: Oct. 10, 2023

(54) METHODS AND SYSTEMS FOR LIMITING WATER WITHIN A PHOTOIONIZATION DETECTOR

(71) Applicant: HONEYWELL INTERNATIONAL INC., Morris Plains, NJ (US)

(72) Inventors: Chuang Huang, Morris Plains, NJ (US); Tengfei Zhang, Morris Plains, NJ (US); Bing Chen, Morris Plains, NJ (US); Feng Liang, Morris Plains, NJ (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 616 days.

(21) Appl. No.: 16/916,287

(22) Filed: Jun. 30, 2020

(65) Prior Publication Data
US 2021/0003542 A1    Jan. 7, 2021

(30) Foreign Application Priority Data

Jul. 1, 2019 (CN) .......................... 201910584530.8

(51) Int. Cl.
*G01N 33/00* (2006.01)
*G01N 27/66* (2006.01)

(52) U.S. Cl.
CPC ......... *G01N 33/0026* (2013.01); *G01N 27/66* (2013.01); *G01N 33/0029* (2013.01)

(58) Field of Classification Search
CPC ........... G01N 33/0026; G01N 33/0029; G01N 33/006; G01N 33/007; G01N 27/66
See application file for complete search history.

(56) References Cited

U.S. PATENT DOCUMENTS

| | | |
|---|---|---|
| 5,701,009 A | 12/1997 | Griffiths et al. |
| 5,773,833 A | 6/1998 | Hsi |
| 6,096,178 A | 8/2000 | Amirav et al. |
| 7,046,012 B2 | 5/2006 | Dean et al. |
| 2012/0252347 A1 | 10/2012 | Chan |
| 2012/0279277 A1 | 11/2012 | Parusel et al. |
| 2013/0276512 A1 | 10/2013 | Bae et al. |

FOREIGN PATENT DOCUMENTS

| | | |
|---|---|---|
| CN | 208109752 U | 11/2018 |
| EP | 2458375 A1 | 5/2012 |
| EP | 3702770 A1 | 9/2020 |
| WO | 2003/046535 A2 | 6/2003 |
| WO | 2005/098413 A1 | 10/2005 |
| WO | 2016/162773 A1 | 10/2016 |
| WO | 2018/022072 A1 | 2/2018 |
| WO | 2019/099044 A1 | 5/2019 |

OTHER PUBLICATIONS

Decision to grant a European patent dated Apr. 6, 2023 for EP Application No. 20183328, 2 page(s).
Extended European Search Report issued in European Application No. 20183328.2 dated Jan. 11, 2021, 7 pages.
Examination Report issued in Australian Application No. 2020201513 dated Nov. 13, 2020, 7 pages.
Communication about intention to grant a European patent received for European Application No. 20183328.2, dated Nov. 22, 2022, 6 pages.
European search report dated Jun 23, 2023 for EP Application No. 23160242, 7 page(s).

*Primary Examiner* — Christopher Adam Hixson
(74) *Attorney, Agent, or Firm* — Alston & Bird LLP

(57) ABSTRACT

Methods and systems for detecting and limiting the water in a photoionization detector are provided. The method may include powering off a lamp configured to ionize particles of air. The method may also include monitoring a signal from the photoionization detector. The signal may be monitored based on a current between a signal electrode and a bias electrode. In an instance the signal is above a signal threshold, the method may also include electrolyzing one or more particles of water present in the photoionization detector by closing a leakage switch in order to allow current to flow through the bias electrode and the signal electrode. In an instance the signal is below the signal threshold, the method may include powering on the lamp to begin photoionization detection. Corresponding systems are also provided.

11 Claims, 8 Drawing Sheets

METHODS AND SYSTEMS FOR LIMITING WATER WITHIN A PHOTOIONIZATION DETECTOR

CROSS-REFERENCE TO RELATED APPLICATIONS

This specification is based upon and claims the benefit of priority from Chinese patent application number CN 201910584530.8 filed on Jul. 1, 2019, the entire contents of which are incorporated herein by reference.

FIELD OF THE INVENTION

The present disclosure relates generally to methods, apparatuses, and systems for limiting water accumulation within a photoionization detector (PID), and more particularly, to methods and systems for detecting and removing water accumulated within a PID.

BACKGROUND

Gas detectors may detect and/or measure the concentration level of compounds in a gaseous substance, including, for example, organic compounds and inorganic compounds. For example, a photoionization detector (PID) is a gas detector that may measure the concentration level of volatile organic compounds in a gaseous substance. The term "volatile organic compound" (or "VOC") refers to organic compounds that may have a high vapor pressure at ordinary room temperature (i.e. they may easily become gases or vapors). Example chemicals in example volatile organic compounds may include, for example, formaldehyde, methane, and benzene.

Generally, a PID consists of a short-wavelength ultraviolet (UV) lamp shining onto a small cell containing a gas sample. Within the cell is a set of electrodes that have an electrical potential applied. The UV light photoionizes trace organic compounds, but not the air, resulting in electrons being ejected and forming positively charged molecules. The electrons and positive ions are propelled to the electrodes and the resulting current is proportional to the gas or vapor concentration. In general, any compound with ionization energy (IE) lower than that of the lamp photons can be measured. A high-level concentration of volatile organic compounds in indoor air or outdoor air may cause adverse effect on health and environment. As such, PIDs may be utilized to measure and monitor the concentration level of volatile organic compounds in various indoor and/or outdoor locations.

As an industrial sensor, PIDs may face high humidity environments. The humidity may cause some example problems, such as sensor leak. The high humidity may also cause current measurements between a signal electrode and a bias electrode during operation that cause sensor inaccuracy. Through applied effort, ingenuity, and innovation, many of these identified problems have been solved by developing solutions that are included in embodiments of the present disclosure, many examples of which are described in detail herein.

BRIEF SUMMARY

Various embodiments described herein relate to methods, apparatuses, and systems for providing limiting water accumulation within a PID. In an example embodiment, a method of detecting water in a photoionization detector is provided. The method includes monitoring a signal from the photoionization detector. The signal is monitored based on a current between a signal electrode and a bias electrode. The method also includes electrolyzing one or more particles of water present in the photoionization detector by closing a leakage switch in order to allow current to flow through the bias electrode and the signal electrode in an instance in which the signal is above a signal threshold.

In some embodiments, the method also includes powering off a lamp configured to ionize particles of air. In some embodiments, the method further includes powering on a lamp configured to ionize particles of air in an instance the signal falls below the signal threshold. In some embodiments, the one or more particles of water present in the photoionization detector are electrolyzed within a housing of the photoionization detector.

In some embodiments, closing a leakage switch is configured to connect a signal electrode to at least one of a reference voltage or a ground in order to allow current to flow through a bias electrode and a signal electrode. In some embodiments, the leakage switch is configured in parallel with a signal processing circuitry. In some embodiments, the powering off the lamp includes opening a lamp switch configured to provide power to the lamp.

In some embodiments, the lamp is a short-wavelength ultraviolet (UV) lamp. In some embodiments, the photoionization detector is portable. In some embodiments, the method also includes closing a voltage bias switch configured to provide voltage to a bias electrode in an instance the lamp is powered off. In some embodiments, monitoring the signal from the photoionization detector occurs in an instance in which the lamp is powered off.

In another example embodiment, a water detection system for a photoionization detector is provided. The water detection system includes a signal electrode configured in proximity to a bias electrode such that a current passes from the bias electrode to the signal electrode in an instance in which at least one of organic compound or water is present in the photoionization detector. The water detection system also includes a signal monitor configured to monitor a signal from the system. The water detection system further includes a leakage switch configured to enable a charge to flow through any water present so as to electrolyze in an instance in which the signal is above a signal threshold.

In some embodiments, the water detection system also includes a lamp configured to ionize particles of air. In some embodiments, the water detection system may be further configured to power on the lamp configured to ionize particles of air in an instance the signal falls below the signal threshold. In some embodiments, the one or more particles of water present in the photoionization detector are electrolyzed within a housing of the photoionization detector.

In some embodiments, the leakage switch is configured to connect the signal electrode to at least one of a reference voltage or a ground in order to allow current to flow through the bias electrode and the signal electrode in order to electrolyze one or more particles of water. In some embodiments, the leakage switch is configured in parallel with a signal processing circuitry.

In some embodiments, the water detection system also includes a lamp switch configured to provide power to the lamp, wherein the lamp switch is opened in order to power off the lamp. In some embodiments, the water detection system also includes a voltage bias switch configured to provide voltage to a bias electrode. In such embodiments, the voltage bias switch is closed in an instance the lamp is powered off. In some embodiments, the signal monitor is configured to monitor a signal from the system in an instance in which the lamp is powered off.

The above summary is provided merely for purposes of summarizing some example embodiments to provide a basic understanding of some aspects of the invention. Accordingly, it will be appreciated that the above-described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE DRAWINGS

The description of the illustrative embodiments may be read in conjunction with the accompanying figures. It will be appreciated that, for simplicity and clarity of illustration, elements illustrated in the figures have not necessarily been drawn to scale, unless described otherwise. For example, the dimensions of some of the elements may be exaggerated relative to other elements, unless described otherwise. Embodiments incorporating teachings of the present disclosure are shown and described with respect to the figures presented herein, in which.

DETAILED DESCRIPTION OF THE INVENTION

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

The components illustrated in the figures represent components that may or may not be present in various embodiments of the invention described herein such that embodiments may include fewer or more components than those shown in the figures while not departing from the scope of the invention. Some components may be omitted from one or more figures or shown in dashed line for visibility of the underlying components.

The phrases "in an example embodiment," "some embodiments," "various embodiments," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "example" or "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that a specific component or feature is not required to be included or to have the characteristic. Such component or feature may be optionally included in some embodiments, or it may be excluded.

As described above, example PIDs may accumulate water due to condensation and humidity. Additionally, heating up the sensor in order to remove the water using conventional methods may require large and/or inefficient amounts of energy. As such and as water in the PID may affect the signal reading during operation, removing the water may be useful for ensuring the accuracy and precision of the PID. Various example embodiments of the present disclosure may eliminate the water present within a PID, allowing for a consistent signal reading while remaining energy efficient.

Figure 1:
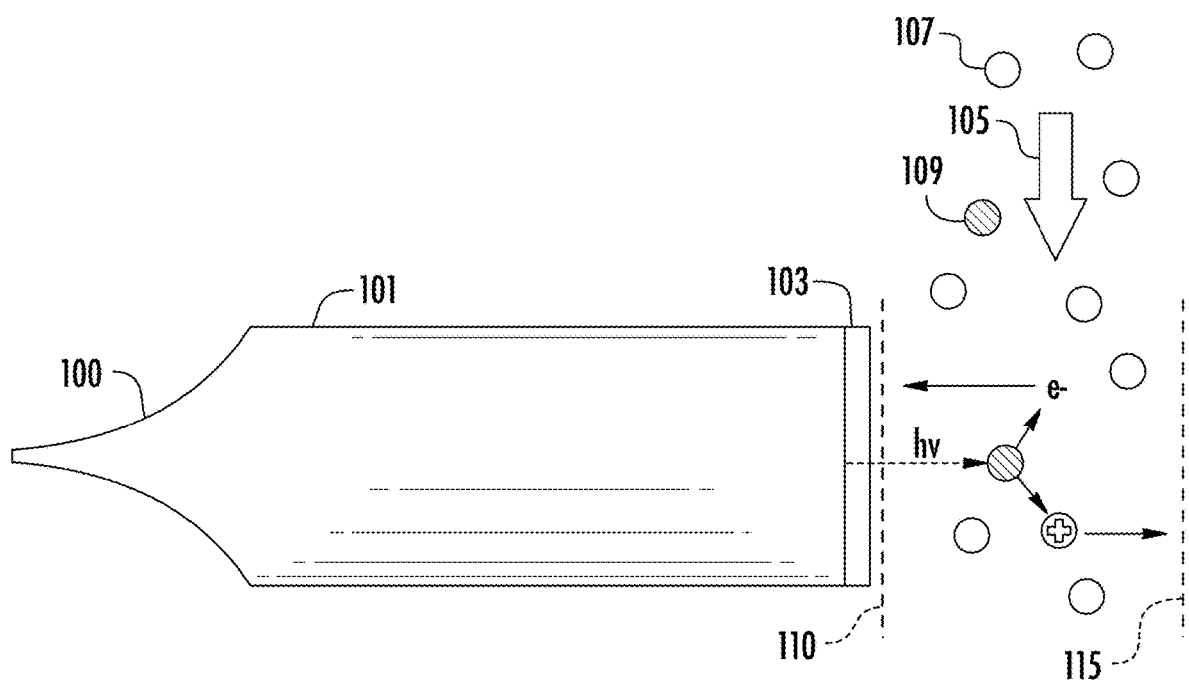
FIG. 1 illustrates an example schematic diagram showing an example photoionization detector lamp in accordance with various embodiments of the present disclosure.

Referring now to FIG. 1, an example schematic diagram showing an example photoionization detector lamp 100 in accordance with various embodiments of the present disclosure is provided. In particular, the example photoionization detector lamp 100 may comprise a glass tube member 101, and a window member 103.

In some examples, the glass tube member 101 may comprise a gaseous substance or a combination of gaseous substances, which may include but are not limited to, inert gases such as argon (Ar), xenon (Xe), and/or krypton (Kr). In some embodiments, a single gas maybe used in the glass tube member 101. Alternatively, mixed gases may be used in the glass tube member 101. The number of gases and the type of gases in the glass tube member 101 may be desired energy level of the UV lamp. The gaseous substance(s) within the glass tube member 101 may be excited through any of a variety of excitation methods to produce an ultraviolet (UV) light source. For example, a voltage (e.g. an alternating current (AC) voltage) may be supplied to the glass tube member 101. In such examples, the AC voltage may cause ionization of the gaseous substance(s) within the glass tube member 101, resulting in a glow discharge. The glow discharge associated with the plasma may emit a low-wavelength ultraviolet (UV) light.

Referring back to FIG. 1, ultraviolet light may be transmitted through the window member 103. In some examples, the window member 103 may comprise material(s) that enables and/or facilitates transmissions of low-wavelength ultraviolet light, including, for example, salt crystal materials. As the ultraviolet light passes through the window member 103, molecules in the gaseous substance may be exposed to the ultraviolet light and detected by the photoionization detector.

In some example embodiments, the photoionization detector may be configured to detect, for example, volatile organic compound (VOC) in the air. In this regard, an anode element (e.g., bias electrode 110) and a cathode element (e.g., signal electrode 115) are provided. In some examples, the anode element may be an electrode that attracts negatively charged electrons. In some examples, the cathode element may be an electrode that attracts positively charged electrons.

As shown in FIG. 1, the air may flow through the photoionization detector in a direction as indicated by arrow 105. The air may comprise VOC molecules 109 and non-VOC molecules 107. As VOC molecules 109 and non-VOC molecules 107 pass through the photoionization detector, they may be exposed to the ultraviolet light generated by the photoionization detector lamp 100. In particular and as is shown in FIG. 1, the ultraviolet light may cause photoionization of the VOC molecules 109, which may result in electrons of the VOC molecules 109 being ejected and forming positively charged ions. The electrons may travel to the anode element (e.g., bias electrode 110), while the positively charged ions may travel to the cathode element (e.g., signal electrode 115). As the electrons and the positively charged ions are propelled to the corresponding electrodes, an electric current may be generated.

In contrast, the ultraviolet light may not cause photoionization of the non-VOC molecules (e.g., non-VOC air) 107 and, as a result, the non-VOC molecules 107 do not generate electric current. In other words, the electric current generated through the ultraviolet light photoionization is proportional to the amount of VOC molecules 109 in the air. As such, the concentration level of the volatile organic compounds (VOC) may be determined, in some examples by the photoionization detector based at least in part on the electric current.

In some example embodiments, the photoionization detector relies at least in part on the photoionization of the molecules caused by the ultraviolet light that is generated by the photoionization detector lamp. However, for the photoionization detector to operate within expected tolerances, fake signals created from noise and/or leakage from other sources need to be removed, limited, or accounted for by the PID. Specifically, water accumulating in the system due to high humidity or the like may case inaccurate voltage readings. In this regard, various embodiments of the present disclosure may be embodied as systems and apparatuses for limiting or otherwise eliminating water within a PID lamp 100.

Figure 2:
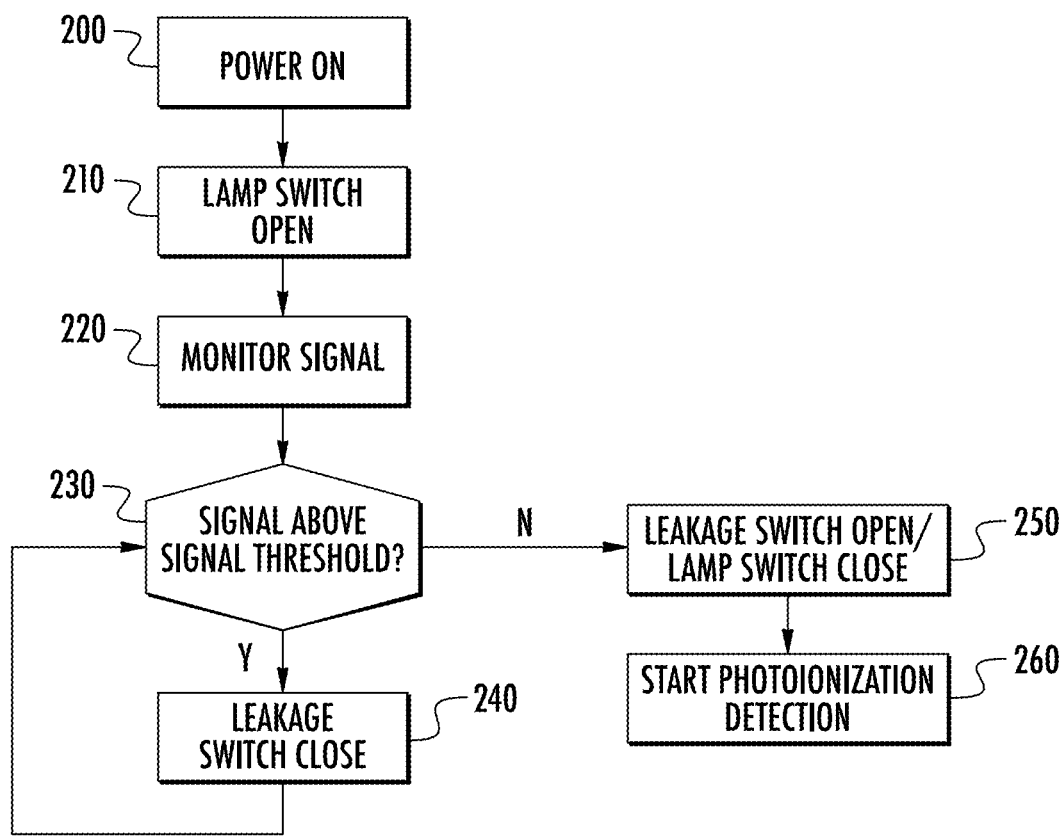
FIG. 2 is a flowchart illustrating the operations of a PID in accordance with various embodiments, such as FIGS. 3-5 of the present disclosure.
Figure 3:
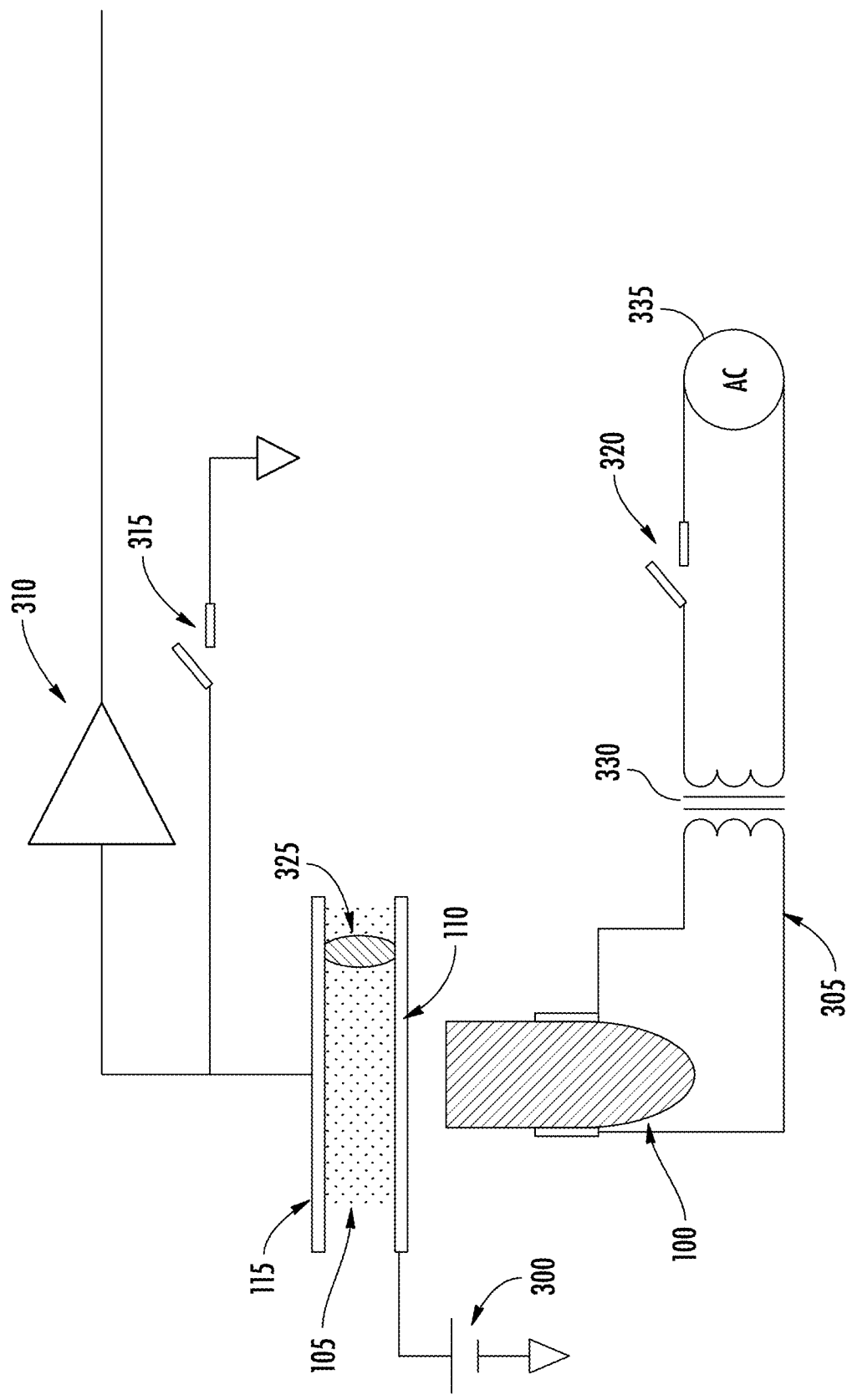
FIG. 3 illustrates a PID circuit diagram configured with a water detection system in accordance with an example embodiment of the present disclosure.
Figure 4:
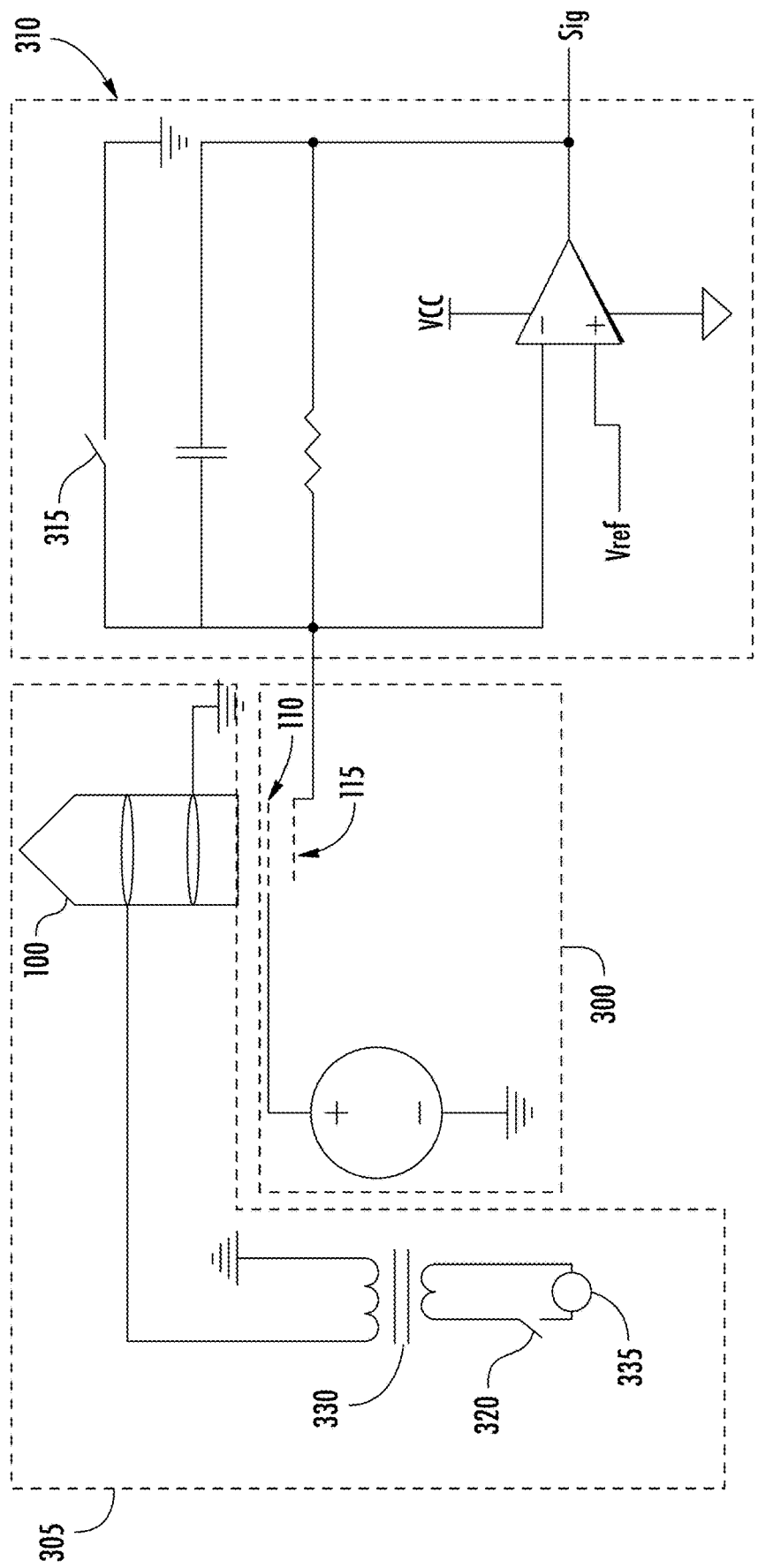
FIG. 4 illustrates another PID circuit diagram configured with a water detection system in accordance with an example embodiment of the present disclosure.
Figure 5:
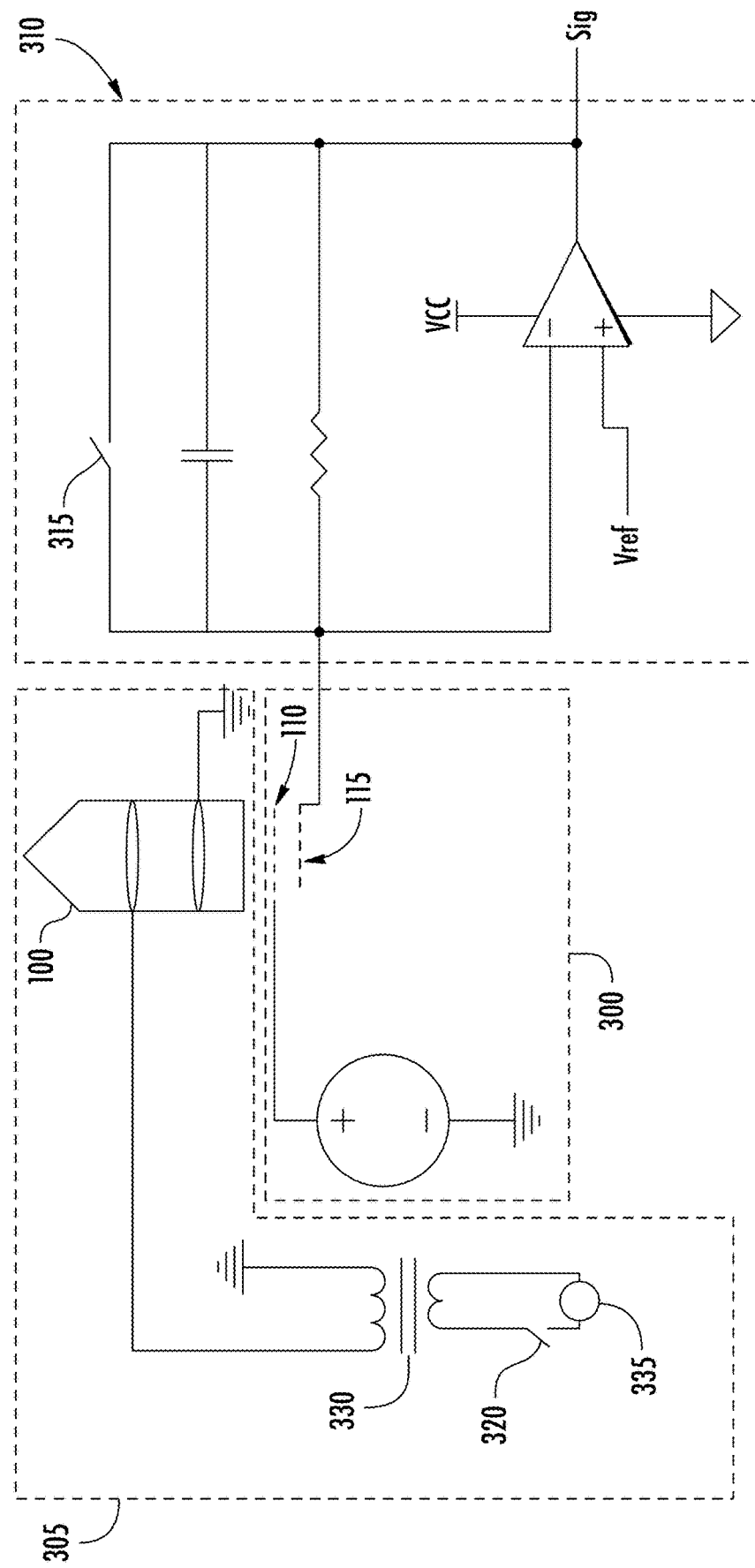
FIG. 5 illustrates still another PID circuit diagram configured with a water detection system in accordance with an example embodiment of the present disclosure.

Referring now to FIG. 2, a flowchart of the operations of a photoionization detector for detecting and removing water within the PID with two switches in accordance with example embodiments, such as PID circuitry diagrams shown in FIGS. 3-5, is provided. Unless explicitly stated otherwise, the operations of FIG. 2 may be carried out by each PID circuit diagram shown in FIGS. 3-5. Referring to Block 200 of FIG. 2, the method includes powering on the photoionization detector. In some embodiments, the PID may already be powered (e.g., the operations may be completed intermittently during operation).

Referring now to Block 210 of FIG. 2, the method includes opening the lamp switch 320 to power off the lamp 100. In some embodiments, the lamp 100 may be configured to operate in the same way as the lamp 100 described in FIG. 1. In an instance in which the lamp 100 is powered off, the photoionization may cease, and the current created by said photoionization also ceases. In some embodiment, the lamp switch 320 may be configured to complete the lamp drive circuitry 305. As shown in FIG. 3, for example, the lamp switch 320 may be configured to complete the lamp drive circuitry 305, such that the lamp receives voltage from a power source. In some embodiments, the lamp switch 320 may be an analog switch realized by an integrated circuit, a simple metal-oxide-semiconductor field-effect transistor (MOSFET) circuit, or another circuit realized by discrete components. As discussed above in reference to FIG. 1, in an instance the lamp is powered on, the VOC molecules passing through the lamp may be photoionized creating an electrical connection between the bias electrode 110 and the signal electrode 115. In an instance in which the lamp 100 is powered off, the photoionization of VOC molecules may cease and the electrical connection between the bias electrode 110 and the signal electrode will end. In some examples, however, the electrical connection between the bias electrode 110 and the signal electrode may not end if water is present in the PID.

Referring now to Block 220 of FIG. 2, the method includes monitoring the signal of the photoionization detector. In some embodiments, the signal monitored may be the current, voltage, or the like. In some embodiments, signal may be determined by an analog-to-digital convertor (ADC). For example, the ADC may read the changing voltage and output a signal indicating the voltage value. In some embodiments, the monitoring of the signal may be completed by the signal processing circuitry 310 (e.g., an ADC may be a part of the signal processing circuitry 310). In some embodiments, the monitoring may be activated after the lamp 100 has been powered off.

Referring now to decision Block 230 of FIG. 2, the photoionization sensor, such as via a processor or the like, determines whether the signal is above a signal threshold. In some embodiments, the signal of the PID (e.g., voltage) may be at or near zero when the lamp 100 is powered off. In an example embodiment, the water detection system may be configured to determine whether any substantial rises in the signal of the PID occur while the lamp 100 is powered off. For example, an ADC may be configured to read the signal value and a processor may be configured to determine whether the signal is above the signal threshold. In some embodiments, the signal threshold may be based on the PID device resolution during operation. For example, the signal threshold may be from 3 millivolts to 300 millivolts in an instance in which the device resolution is 0.3 mV. In some embodiments, the device resolution and/or the signal threshold may be used for different gas concentration level. In some embodiments, the water detection system may be configured with a signal threshold, such that a signal above said threshold may indicate that water is in the system. In some embodiments, the signal threshold may be set based on the amount of water allowed in the PID, the precision of monitoring components, and/or the like. For example, the amount of signal increase may be correlated to the amount of water present in the PID.

Referring now to Block 240 of FIG. 2, in an instance in which the signal is determined as being above the signal threshold, the leakage switch 315 is closed. As shown in FIGS. 3 and 4 and in some example embodiments, closing the leakage switch 315 connects the signal electrode 115 to a ground. In some embodiments, the leakage switch 315 may be an analog switch realized by an integrated circuit, a simple metal-oxide-semiconductor field-effect transistor (MOSFET) circuit, or another circuit realized by discrete components. In some embodiments, such as FIG. 5, closing the leakage switch 315 connects the signal electrode 115 to a reference voltage. In some embodiments, the leakage switch 315 connecting the signal electrode 115 to a ground (e.g., FIGS. 3 and 4) or reference voltage (e.g., FIG. 5) may allow current to flow from the bias electrode 110, which is connected to the DC Bias Voltage 300, into the signal electrode 115, in an instance in which water is present in the PID.

In some embodiments, such as the embodiment shown in FIG. 5, the leakage switch 315 may be configured in parallel with the signal processing circuitry 310. In an instance in which the leakage switch 315 is closed, a current is passed through the water 325 present in the PID causing the water to be electrolyzed (e.g., $H_2O$ is converted into $H_2$ and $O_2$). In some embodiments, the converted $H_2$ and $O_2$ may be carried out of the PID much like other gases through a PID outlet. For example, the PID may be configured with a gas pathway 205 which has an inlet and an outlet at each end of the PID, such that the converted $H_2$ and $O_2$ continue out of the PID through the outlet of the PID. In some embodiments, after the water in the PID has been electrolyzed, the signal of the system (e.g., the current or voltage) may be monitored to determine whether the signal is now below the signal threshold indicating that the water has been eliminated.

In some example embodiments, the monitoring of the signal (e.g., such as is shown in block 220) may continue during the electrolyzing process. In some examples the electrolyzing may be stopped once the signal goes below the signal threshold. Whereas in alternative embodiments, the signal may not be monitored during the electrolyzing and the monitoring may resume after the leakage switch 315 is opened. In yet further alternative embodiments, the leakage switch 315 may be closed for a set amount of time (e.g., 5 seconds). In various embodiments, the signal may be monitored during and/or after the electrolyzing process to determine whether the signal is still above the signal threshold.

Referring now to Block 250 of FIG. 2, in an instance in which the signal is below the signal threshold, the leakage switch is opened or remains open and the lamp switch is closed. That is, in an instance in which the initial signal is below the signal threshold, the minimum amount of water to electrolyze the water is not present in the PID. In some embodiments, where the signal threshold has previously been monitored as being above the signal threshold, the leakage switch 315 will remain open. In some embodiments, where the leakage switch 315 had been previously closed (e.g., water has already been electrolyzed by the PID), the leakage switch 315 may be opened. In some embodiments and in an instance in which the signal is below the signal threshold, the lamp switch 320 may be closed so as to power on the lamp.

Referring now to Block 260 of FIG. 2, in an instance in which the lamp switch 315 is closed, the photoionization detection resumes. In some embodiments, the lamp switch being closed powers on the lamp 100 and, subsequently, allows for the performance of photoionization detection by the PID. In some embodiments, the operations shown in FIG. 2 may be repeated, such as in regular intervals. In some embodiments, the operations shown in FIG. 2 may be repeated based on user input (e.g., a user may be able to activate the water detection system). In various embodiments, the regularity of water detection may additionally or alternatively be based on the environment used, the water level tolerance, PID operations (e.g., the water detection system may be activated during low usage time periods of the PID), and/or the like.

Referring now to FIGS. 3-5, circuit diagrams are provided in accordance with various example embodiments of the present disclosure. Unless otherwise stated, various circuitry configurations may be used, for example, any combination of the example circuits discussed herein may be relied upon to remove water from the PID.

Referring now to FIG. 3, a simplified PID circuit diagram is shown in accordance with an example embodiment. In various embodiments, the lamp drive circuitry 305 may include a power source 335 (e.g., alternating current (AC) power source), a lamp switch 320, a lamp drive transformer 330 configured to convert AC into direct current (DC) and a lamp 100. Additionally, the PID may have a bias electrode 110 configured in proximity to the lamp and in electrical communication with the DC Bias Voltage 300. In some embodiments, the PID may also have a gas pathway 105 defined between the bias electrode 110 and the signal electrode 115. Additionally, the signal electrode 115 may be connected to the signal processing circuitry 310 and a leakage switch 315, which may be connected to a ground as is shown in FIG. 3. In an instance in which the leakage switch 315 closes, current is generated between the bias electrode 110 and the signal electrode 115, such that water (e.g., water 325) present in the PID may be electrolyzed. In some embodiments, the quality of the leakage switch 315 may affect the time required to electrolyze any water present in the PID. For example, a higher quality leakage switch may allow for quicker electrolyzing of the water present in the PID.

Referring now to FIG. 4, a PID circuit diagram is shown in accordance with an example embodiment. In various embodiments, the lamp drive circuitry 305 may include a power source 335 (e.g., alternating current (AC) power source), a lamp switch 320, a lamp drive transformer 330 configured to convert AC into direct current (DC) (e.g., the DC voltage may be relatively low from 3 to 30 Volts, while the AC voltage is relatively high from 200 to 2000 Volts), and a lamp 100. In some embodiments, the lamp switch 320 may be configured to allow the lamp 100 to be powered in an instance the lamp switch 320 is closed. Additionally, the PID may have a bias electrode 110 configured in proximity to the lamp 100 and in electrical communication with the DC Bias Voltage 300. In some embodiments, the DC Bias Voltage may be from 10 to 100 Volts. In some embodiments, the PID may also have a gas pathway defined between the bias electrode 110 and the signal electrode 115. Additionally, the signal electrode 115 may be connected to the signal processing circuitry 310, including a leakage switch 315, which may be connected to a ground as is shown in FIG. 4. In an instance in which the leakage switch 315 closes, current is generated between the bias electrode 110 and the signal electrode 115, such that water present in the PID may be electrolyzed. In some embodiments, the signal processing circuit 310 may also include an op-amp, a resistor (e.g., a 1 megohm to 1 gigaohm resistor), and a capacitor (e.g., a 100 picofarad to 100 nanofarad capacitor) for monitoring the PID. In some embodiments, the op-amp, the resistor, and the capacitor operate with a high impedance, such that the signal of the system is low in an instance in which the lamp is powered off. In some embodiments, the signal processing circuit 310 may also include a microcontroller and/or integrated circuit. In such embodiments, the microcontroller and/or integrated circuit may allow the signal processing circuit 310 to integrate the signal inside of the PID. In some embodiments, the signal may be inputted directly to the signal processing circuit 310.

Referring now to FIG. 5, a PID circuit diagram is shown in accordance with an example embodiment. In various embodiments, the lamp drive circuitry 305 may include a power source 335 (e.g., alternating current (AC) power source), a lamp switch 320, a lamp drive transformer 330 configured to convert AC into direct current (DC) (e.g., the DC voltage may be relatively low from 3 to 30 Volts, while the AC voltage is relatively high from 200 to 2000 Volts), and a lamp 100. Additionally, the PID may have a bias electrode 110 configured in proximity to the lamp 100 and in electrical communication with the DC Bias Voltage 300. In some embodiments, the DC Bias Voltage may be from 10 to 100 Volts. In some embodiments, the PID may also have a gas pathway defined between the bias electrode 110 and the signal electrode 115. Additionally, the signal electrode 115 may be connected to the signal processing circuitry 310, including a leakage switch 315. In some embodiments, the leakage switch 315 may be configured in parallel with the signal processing circuitry 310, as is shown in FIG. 5. In an instance in which the leakage switch 315 closes, current is generated between the bias electrode 110 and the signal electrode 115, such that water present in the PID may be electrolyzed. In some embodiments, the signal processing circuit 310 may also include an op-amp, a resistor (e.g., a 1 megohm to 1 gigaohm resistor), and a capacitor (e.g., a 100 picofarad to 100 nanofarad capacitor). In some embodiments, the op-amp, the resistor, and the capacitor operate with a high impedance, such that the signal of the system is low in an instance in which the lamp is powered off. In some embodiments, the signal processing circuit 310 may also include a microcontroller and/or integrated circuit. In such embodiments, the microcontroller and/or integrated circuit may allow the signal processing circuit 310 to integrate the signal inside of the PID. In some embodiments, the signal may be inputted directly to the signal processing circuit 310.

Figure 6:
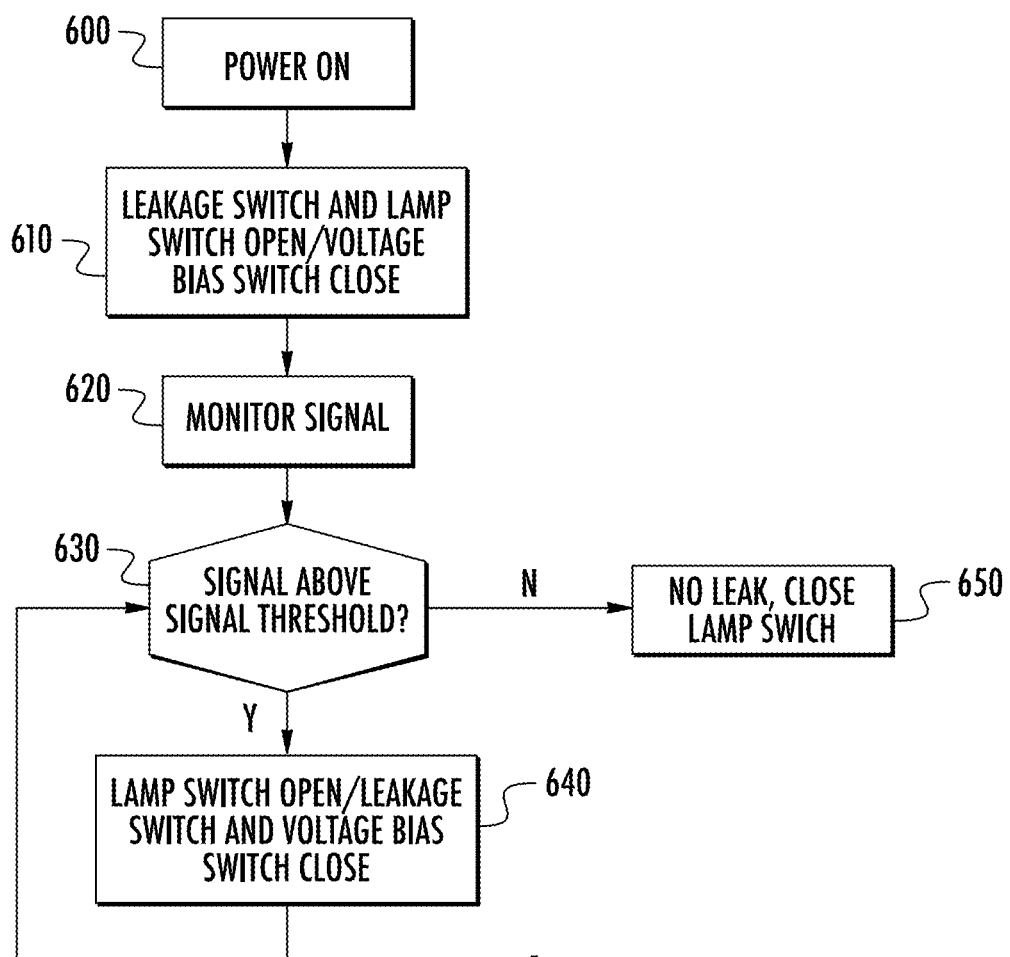
FIG. 6 illustrates another flowchart illustrating the operations of a PID in accordance with various embodiments, such as FIG. 7, of the present disclosure.
Figure 7:
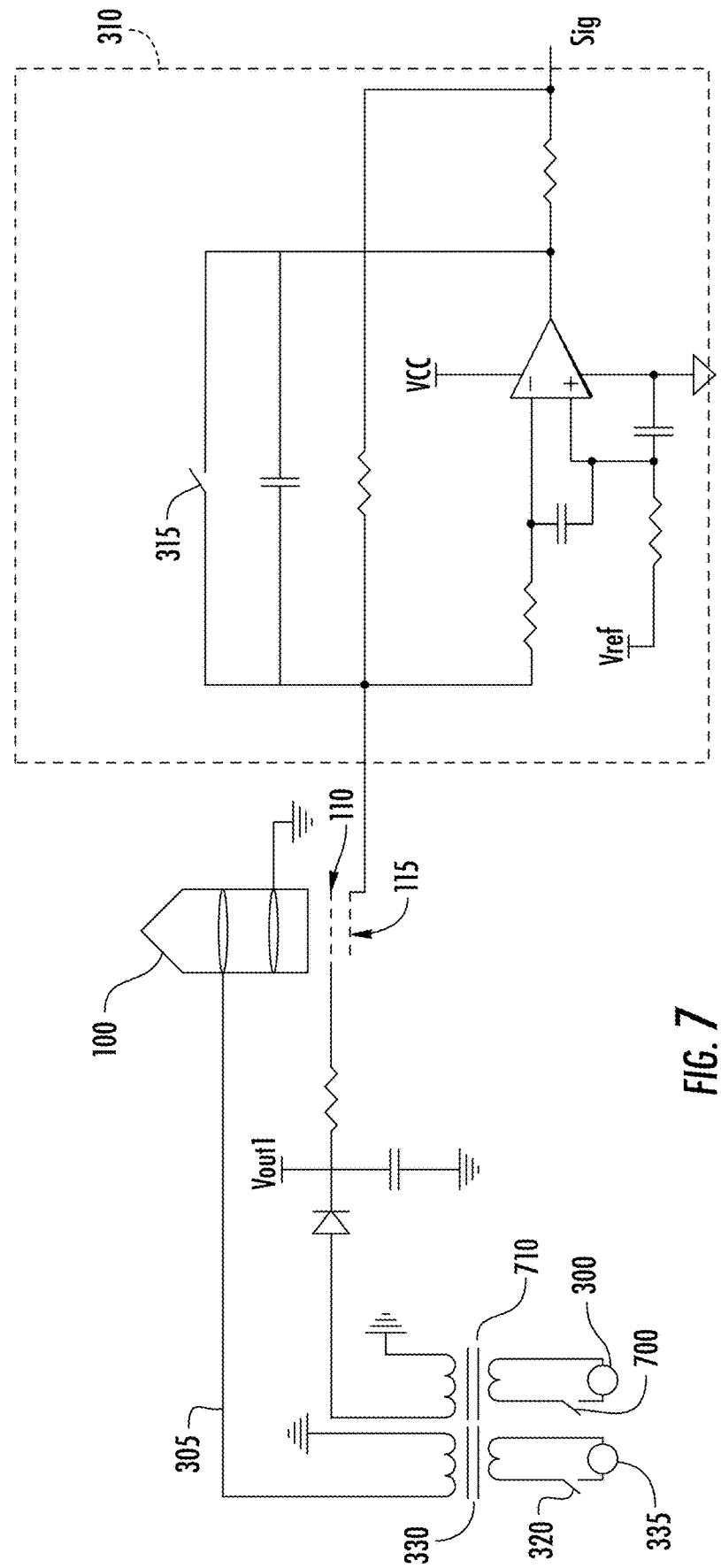
FIG. 7 illustrates another PID circuit diagram configured with a water detection system in accordance with an example embodiment of the present disclosure.

Referring now to FIG. 6, another flowchart of the operations of a photoionization detector for detecting and removing water within the PID with three switches in accordance with an example embodiment, such as the PID circuitry diagram shown in FIG. 7, is provided. The PID circuit diagram of FIG. 7 may be configured with a lamp switch configured to power the lamp 100, a Bias Voltage Switch 700 configured to electrically connect the DC Bias Voltage 300 to the Bias Electrode 110, and a leakage switch 315 configured to electrolyze the water in the PID. Referring to Block 600 of FIG. 6, the method includes powering on the photoionization detector. The operations of Block 600 may be the same as discussed for Block 200 of FIG. 2 above.

Referring now to decision Block 610 of FIG. 6, the method includes opening or leaving open the leakage switch 315 and the lamp switch 320, while closing or leaving closed the voltage bias switch 700. In some embodiments, the voltage bias switch 700 may be an analog switch realized by an integrated circuit, a simple metal-oxide-semiconductor field-effect transistor (MOSFET) circuit, or another circuit realized by discrete components. In some embodiments, the leakage switch 315 may remain open during the operations of Block 610. In some embodiments, the voltage bias 700 may already be closed and the voltage bias switch may remain closed, while the lamp switch 320 is closed. In some embodiments, the opening and/or closing of the various switches may be completed at once or in series in accordance with the systems and methods disclosed herein.

Referring now to Block 620, the method includes monitoring the signal of the PID while the lamp switch 320 is open and the voltage bias switch is closed. In various embodiments, the monitoring of the signal may be the same as discussed in reference to Block 220 of FIG. 2, discussed above. Referring now to decision Block 630 of FIG. 6, the method includes determining whether the signal is above a signal threshold. The signal threshold may be set as discussed above in reference to decision Block 230 of FIG. 2.

In some embodiments, the method may also include monitoring the signal of the PID when all three of the leakage switch 315, the lamp switch 320, and the voltage bias switch 700 are opened. In some embodiments, a signal processing circuit 310 fault may generate fake signal. In an instance in which the leakage switch 315, the lamp switch 320, and the voltage bias switch 700 are open, a non-zero signal may indicate that the signal processing circuit 310 fault. In some embodiments, an error message may be displayed (visually, audibly, tactically, or the like) based on the potential signal processing circuit 310 fault.

Referring now to Block 640 of FIG. 6, in an instance the signal is above the signal threshold, the lamp switch 320 remains opened, while the leakage switch 315 is closed and the voltage bias switch 700 remains closed. In various embodiments, in an instance the signal is above the signal threshold, an undesirable level of water may be present in the PID. In some embodiments, such as the PID circuit diagram shown in FIG. 7, in an instance the leakage switch 315 and the voltage bias switch 700 are both closed the water in the PID may be electrolyzed, such discussed herein. In some embodiments, only the water between the bias electrode 110 and the signal electrode 115 may cause a fake signal to be observed. In some embodiments, in an instance in which the leakage switch 315 and the voltage bias switch 700, if applicable, are closed, only the water between the bias electrode 110 and the signal electrode 115 may be electrolyzed as discussed herein.

Referring now to Block 650 of FIG. 6, the method includes closing the lamp switch 320 in an instance the signal is not above the signal threshold. Such as in FIG. 2, the lamp 100 may be powered on when the lamp switch 320 is closed, and the photoionization detection may be activated and/or otherwise resumed. In some embodiments, the operations of FIG. 6 may be repeated intermittently, such as by user input or set periods of time. In some embodiments, the voltage bias switch 700 remains closed allowing the ionization detection to occur.

Referring now to FIG. 7, a PID circuit diagram in accordance with an example embodiment is provided. The PID circuit diagram shown in FIG. 7 may configured to carry out the operations discussed in reference to FIG. 6. a PID circuit diagram is shown in accordance with an example embodiment. In various embodiments, the lamp drive circuitry 305 may include a power source 335 (e.g., alternating current (AC) power source), a lamp switch 320, a lamp drive transformer 330 configured to convert AC into direct current (DC) (e.g., the DC voltage may be relatively low from 3 to 30 Volts, while the AC voltage is relatively high from 200 to 2000 Volts), and a lamp 100. In some embodiments, the lamp switch 320 may be configured to allow the lamp 100 to be powered in an instance the lamp switch 320 is closed.

Additionally, the PID may have a bias electrode 110 configured in proximity to the lamp 100 and in electrical communication with the Bias Voltage 300. In some embodiments, the Bias Voltage 300 may be an AC power source and a bias transformer 710 may be configured to convert the AC into DC. For example, the bias voltage provided to the bias electrode 110 may be in the tens of volts, while in some embodiments, such as portable devices powered by batteries, the bias voltage power source may operate at lower volts and therefore may use a transformer to reach the desired voltage. Additionally, a voltage bias switch 700 may be configured to allow current to reach the bias transformer 710. In some embodiments, the PID may also have a gas pathway defined between the bias electrode 110 and the signal electrode 115. In some embodiments, the signal electrode 115 may be connected to the signal processing circuitry 310, including a leakage switch 315, which may be connected to in parallel with the rest of the signal processing circuit 310. In an instance in which the leakage switch 315 is closed and the voltage bias switch 700 is closed, current is generated between the bias electrode 110 and the signal electrode 115, such that water present in the PID may be electrolyzed. In some embodiments, the signal processing circuit 310 may also include an op-amp, a resistor (e.g., a 1 megohm to 1 gigaohm resistor), and a capacitor (e.g., a 100 picofarad to 100 nanofarad capacitor) for monitoring the PID. In some embodiments, the op-amp, the resistor, and the capacitor operate with a high impedance, such that the signal of the system is low in an instance in which the lamp is powered off.

Figure 8:
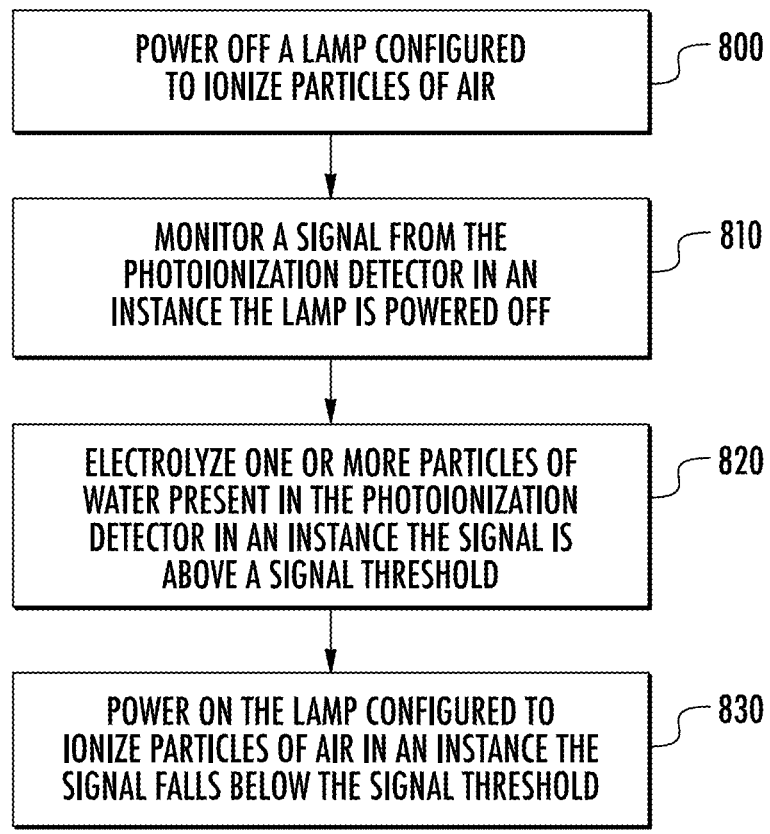
FIG. 8 is another flowchart illustrating the operations of a PID in accordance with various embodiments of the present disclosure.

Referring now to FIG. 8, yet another flowchart illustrating the operations of a photoionization detector for detecting and removing water within the PID in accordance with an example embodiment is provided. The operations discussed herein may include operations discussed in FIGS. 2 and 6, unless explicitly stated otherwise.

Referring now to Block 800 of FIG. 8, the method includes powering off a lamp 100 configured to ionize particles of air. As discussed above, the powering off of the lamp 100 may be achieved by opening the lamp switch 315 connected to the lamp power source 335. Referring now to Block 810 of FIG. 8, the method includes monitoring a signal from the photoionization detector in an instance the lamp is powered off. Various monitoring methods may be used, as discussed in reference to, for example, FIGS. 2 and 6. For example, the signal (e.g., voltage from the signal processing circuit) may be monitored in an instance in which the lamp 100 is powered off (e.g., lamp switch 320 is opened). In various embodiments, the signal may include a current, voltage, or the like. In some embodiments, the signal may be relatively low in an instance that the lamp 100 is powered off and little to no water is present in the PID. For example, the voltage reading may be at or near zero in an instance in which the lamp 100 is powered off and no water is present in the PID. In some embodiments, the signal processing circuit 310 may be configured to monitor the signal at various times, including when the lamp 100 is powered off. In an instance the monitored signal is above a signal threshold (e.g., indicating that a certain amount of water is present in the PID), the PID is configured to electrolyze the water present in the PID.

In some embodiments, the signal first come from the ions and electrons, such as in the water 325. In such an embodiment, the signal may be created by the current passing through the bias electrode 110 and the signal electrode 115. In some embodiments, the signal current may be converted into a signal voltage by the signal processing circuit 310 and the signal voltage may be converted into a digital value, such as by an ADC. In some embodiments, the signal processing circuit 310 may include a microcontroller or the like to process the digital value. For example, the digital value may be processed by the microcontroller through firmware and/or software logic.

Referring now to Block 820 of FIG. 8, the method includes electrolyzing one or more particles of water present in the photoionization detector in an instance the signal is above a signal threshold. The electrolyzing of the water molecules to convert the $H_2O$ to $H_2$ and $O_2$ are discussed above. As discussed above, the electrolyzing of the water molecules may occur in an instance in which current is generated between the bias electrode 110 and the signal electrode 115. In an example embodiment, a current is generated between the bias electrode 110 and the signal electrode 115 in an instance in which water is present and the leakage switch 315 is closed, such that the signal electrode 115 is connected to a ground or reference voltage. Additionally, in some embodiments, the PID may also have a voltage bias switch 700 configured to provide a voltage to the bias electrode 110. In such embodiments, both the voltage bias switch 700 and the leakage switch 315 may need to be closed in order to electrolyze water in the PID.

Referring now to Block 830 of FIG. 8, the method includes powering on the lamp configured to ionize particles of air in an instance the signal falls below the signal threshold. As discussed in reference to FIGS. 2 and 6, the lamp 100 may be powered on by closing the lamp switch 315. In some embodiments, the powering on of the lamp 100 may activate the photoionization detection of the PID, such as through the ionization discussed in reference to FIG. 1.

In various embodiments, one or more of the operations discussed in Block 800 through 830 may be repeated at various times to determine whether water is present in the PID. For example, the water level may be checked every minute or hour of operation. In some embodiments, the length of time required for electrolyzing may depend on the amount of time between water detection and removal. For example, while the monitoring of the signal to determine whether the signal is above a signal threshold may take a similar time to complete (e.g., the water detection ay only take a minute), the electrolyzing of the water within the PID may take longer in an instance the time between water detection is longer (e.g., more water may accumulate, and more water takes longer to electrolyze).

Various embodiments of the present disclosure may be embodied as methods for providing a water detection system within a photoionization detector (PID) lamp. In this regard, FIGS. 2, 7, and 8 each depict a flow diagram illustrating an example method in accordance with various embodiments of the present disclosure. In some examples, each block of the flow diagrams, and combinations of blocks in the flow diagrams, may be implemented by various means such as hardware, firmware, circuitry and/or other devices associated with execution of software including one or more computer program instructions.

In some examples, one or more of the procedures described in FIGS. 2, 7, and 8 may be embodied by computer program instructions, which may be stored by a memory circuitry (such as a non-transitory memory) of a system employing an embodiment of the present disclosure and executed by a processing circuitry (such as a processor) of the system. These computer program instructions may direct the system to function in a particular manner, such that the instructions stored in the memory circuitry produce an article of manufacture, the execution of which implements the function specified in the flow diagram block(s). Further, the system may comprise one or more other circuitries. Various circuitries of the system may be electronically coupled between and/or among each other to transmit and/or receive energy, data and/or information.

In some examples, embodiments may take the form of a computer program product on a non-transitory computer-readable storage medium storing computer-readable program instruction (e.g. computer software). Any suitable computer-readable storage medium may be utilized, including non-transitory hard disks, CD-ROMs, flash memory, optical storage devices, or magnetic storage devices.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

The invention claimed is:

1. A method of detecting water in a photoionization detector, the method comprising:
   monitoring a signal from the photoionization detector, wherein the signal is monitored based on a current between a signal electrode and a bias electrode; and
   in an instance in which the signal is above a signal threshold, electrolyzing one or more particles of water present in the photoionization detector by closing a leakage switch in order to allow current to flow through the bias electrode and the signal electrode.

2. The method of claim 1 further comprising powering off a lamp configured to ionize particles of air.

3. The method of claim 2 further comprising in an instance the signal falls below the signal threshold, powering on a lamp configured to ionize particles of air.

4. The method of claim 1, wherein the one or more particles of water present in the photoionization detector are electrolyzed within a housing of the photoionization detector.

5. The method of claim 1, wherein closing a leakage switch is configured to connect a signal electrode to at least one of a reference voltage or a ground in order to allow current to flow through a bias electrode and a signal electrode.

6. The method of claim 5, wherein the leakage switch is configured in parallel with a signal processing circuitry.

7. The method of claim 2, wherein the powering off the lamp comprises opening a lamp switch configured to provide power to the lamp.

8. The method of claim 2, wherein the lamp is a short-wavelength ultraviolet (UV) lamp.

9. The method of claim 1, wherein the photoionization detector is portable.

10. The method of claim 2 further comprises in an instance the lamp is powered off, closing a voltage bias switch configured to provide voltage to a bias electrode.

11. The method of claim 2, wherein monitoring the signal from the photoionization detector occurs in an instance in which the lamp is powered off.

* * * * *